United States Patent [19]

Voirin et al.

[11] Patent Number: 4,774,067

[45] Date of Patent: Sep. 27, 1988

[54] REGENERATIVE PROCESS FOR REMOVING MERCAPTANS CONTAINED IN A GAS

[75] Inventors: Robert Voirin, Orthez; Jean Elgue, Billere, both of France

[73] Assignee: Societe Nationale Elf Aquitaine (Production), Paris, France

[21] Appl. No.: 13,976

[22] PCT Filed: May 6, 1986

[86] PCT No.: PCT/FR86/00157

§ 371 Date: Jan. 2, 1987

§ 102(e) Date: Jan. 2, 1987

[87] PCT Pub. No.: WO86/06649

PCT Pub. Date: Nov. 20, 1986

[30] Foreign Application Priority Data

May 10, 1985 [FR] France ................. 85 07121

[51] Int. Cl.$^4$ .................... B01J 8/00; C10B 17/00; C10B 17/16; C10B 31/20
[52] U.S. Cl. .................... 423/244; 423/230; 423/245
[58] Field of Search .......... 423/244 A, 244 R, 242 A, 423/242 R, 245 S, 230

[56] References Cited

U.S. PATENT DOCUMENTS

| | | | |
|---|---|---|---|
| 2,259,409 | 10/1941 | Wenzel et al. | 423/230 |
| 2,551,905 | 5/1951 | Robinson | 423/230 |
| 2,747,968 | 5/1956 | Piqache | 423/230 |

FOREIGN PATENT DOCUMENTS 1078828 8/1967 United Kingdom .

OTHER PUBLICATIONS

Chemical Abstracts, vol. 73, 100679d, p. 115, Nov. 1970.

Primary Examiner—Gregory A. Heller
Attorney, Agent, or Firm—Burgess, Ryan & Wayne

[57] ABSTRACT

A regenerative process is provided for removing mercaptans contained in a gas by means of an absorbing agent based on at least one metal oxide capable of chemically fixing the mercaptans. The process comprises an absorption step to fix the mercaptans on the absorbing agent and a regeneration step for regenerating the absorbing agent laden with sulphur-containing products resulting from said fixation. The regeneration is carried out by sweeping the absorbing agent with a hot inert gas to bring the absorbing agent to a temperature between 250° and 500° C. and desorb the sulfur-containing products, and by contacting the absorbing agent thus treated with a gas containing free oxygen to reoxidize the absorbing agent and by cooling the reoxidized absorbing agent by sweeping with a cold inert gas.

21 Claims, 3 Drawing Sheets

FIG_1

REGENERATIVE PROCESS FOR REMOVING MERCAPTANS CONTAINED IN A GAS

The invention concerns a regenerative process for removing mercaptans contained in a gas by means of an absorbing agent based on at least one active metal oxide, that is, susceptible of retaining the mercaptans by chemical action. The invention more particularly refers to an improvment on the regeneration of the absorbing agent that has fixed the mercaptans.

It is known that gases of different origins, specially natural gases, synthesis gases or also residual gases contain by way of impurities small concentrations of mercaptans and that it is necessary to eliminate said mercaptans due to their extremely unpleasant odor and mainly to their toxicity prior to sending said gases either toward the circuits of use of these gases, specially in the case of natural gases or synthesis gases, or also toward the atmosphere in case of residual gases.

Among the processes proposed for removing the mercaptans contained in a gas, there is known a regenerative process that makes use of a solid absorbing agent based on an active metal oxide such as cupric oxide for retaining the mercaptans by formation of mercaptides, said process being particularly adpated for the treatment of natural gases containing mercaptans, since it is not disturbed by the presence of hydrocarbons.

This regenerative process includes an absorption step in the course of which the gas to be treated is brought into contact with the solid absorbing agent at temperatures below 100° C. for retaining the mercaptans on the absorbing agent, a regeneration step in the course of which the absorbing agent that has retained the mercaptans is swept by means of a gas containing free oxygen while operating at temperatures of from 200° C. to 280° C., thereafter the absorbing agent is treated by steam under pressure and by ammonia after which said absorbing agent is washed with hot water and dried and the dried absorbing agent is subjected to an oxidation by a gas containing free oxygen at a temperature of about 200° C., and a cooling step in the course of which the regenerated absorbing agent is brought to an appropriate temperature below 100° C. for being re-used in the absorption step.

A first inconvenience in such a process is the complexity of the operation of regeneration of the absorbing agent, which makes difficult an industrial use of the process. A second inconvenience of said process results from the fact that the first phase of the regeneration operation, namely, the sweeping of the absorbing agent that has retained the mercaptans by a gas containing free oxygen at temperatures of from 200° C. to 280° C., leads to the formation of metallic sulfate, specially copper sulfate, which accumulates inside the absorbing agent and causes a quick reduction of the activity of the latter, which reduces the performances of the process.

There have now been found particular conditions for carrying out the regeneration of the absorbing agent that has retained the mercaptans, which prevent the formation of metallic sulfate and which greatly simplifies the regeneration.

The regeneration according to the invention of the absorbing agent that has retained the mercaptans is easy to carry out and in addition results in maintaining in the time of activity of the regenerated absorbing agent a high value and as result of that an elevated level of performance of the process.

Therefore, the invention proposes a regenerative process for the removal of the mercaptans contained in a gas by making use of a solid absorbing agent based on at least one active metallic oxide, that is, susceptible of retaining the mercaptans by chemical action, said process being of the type including an absorption step in the course of which the gas to be treated is brought into contact with said absorbing agent, while operating at temperatures below 100° C. for retaining the mercaptans on the absorbing agent, and a step of regeneration and of cooling in the course of which the absorbing agent subjected to the regeneration is swept with a gas containing free oxygen for reoxidizing the absorbing agent and thus regenerating it, and the regenerated absorbing agent is cooled to an appropriate temperature for re-use in the absorption step, characterized by carrying out the step of regeneration and of cooling by first bringing the absorbing agent that has retained the mercaptans to a temperature comprised between 250° C. and 500° C., preferably between 300° C. and 450° C., by sweeping with an inert hot gas and continuing said sweeping substantially at said temperature until the absorbing agent contains no more sulfurated compounds, thereafter putting the gas containing free oxygen in contact with the absorbing agent free of sulfurated compounds, while operating at temperatures below 500° C. until complete reoxidation of the absorbing agent, and carrying out at least the last phase of the cooling of the regenerated absorbing agent with an inert gas for removing the oxygen that said regenerated absorbing agent can contain prior to being re-used in the absorption step.

The active metal oxide or the active metal oxides that the absorbing agent can contain are specially selected among the oxides of metals such as copper, zinc, cadmium, mercury, iron, cobalt, silver, platinum and lead.

The process according to the invention is advantageously used in the treatment of different gases, particularly natural gases, synthesis gases or even residual gases that contain by way of impurities a small amount of mercaptans having from 1 to 8 carbon atoms, preferably from 1 to 6 carbon atoms, in their molecule, said mercaptans being compounds of the formula RSH wherein R designates a hydrocarbonated radical, preferably an alkyl radical having $C_1$ to $C_8$, preferably $C_1$ to $C_6$.

According to the invention, by "small amount" is understood a total amount of mercaptans representing at most 2% by volume of the gas to be treated.

The absorbing agent based on active metal oxide used for retaining the mercaptans is advantageously constituted of at least one active metal oxide associated with an inert porous support, said support being in particular a porous metal oxide unreactive with the mercaptans and preferably consists of alumina. The absorbing agent based on an active metal oxide advantageously has a specific surface determined by the method of nitrogen absorption called BET method, of from 10 to 500 $m^2/g$, preferably from 100 to 300 $m^2/g$.

The absorbing agent can be prepared by making use of any known technique that makes it possible to form a close association of at least one active metal oxide and one inert porous carrier. It is possible, for example, to impregnate the selected carrier with one or more salts that generate the metal oxide or the active metal oxides by calcination, then to dry the impregnated carrier and calcining the dried product at a temperature comprised between 300° C. and 600° C. It is also possible to associate the active metal oxide or the active metal oxides with the carrier by coprecipitation techniques followed by drying and calcination in the above mentioned temperature range or also by mixing the active metal oxide or the active metal oxides and the carrier in divided form.

The total amount of active metal oxide present in the absorbing agent can vary broadly. This amount can advantageously range from 1 to 30%, and preferably from 5 to 20%, by weight of the absorbing agent.

As indicated above, the absorption step, in the course of which the gas to be treated is put into contact with the absorbing agent, is carried out at temperatures below 100° C., said temperatures being in particular from 5° to 70° C. and preferably being in the neighborhood of the room temperature, for instance, from 20° C. to 50° C.

The pressures used in the absorption step are not critical. The absorption is generally carried out at the pressure at which the gas to be treated is available. The pressures used in the absorption step can range from a few bars, as for example from 2 to 5 bars for the treatment of a residual gas or of a synthesis gas, to several tens of bars, as for example from 40 to 80 bars in the case of treatment of a natural gas.

The period of contact of the gas to be treated with the absorbing agent must be sufficient to allow an almost complete fixation of the mercaptans by the absorbing agent. The appropriate values of said period of contact can range from 0.5 to 10 seconds, preferably from 0.8 to 6 seconds TPN, which corresponds to VVH values going from 7200 to 360 $h^{-1}$, preferably from 4500 to 600 $h^{-1}$.

In the course of the absorption step the RSH mercaptans contained in the gas to be treated react with the active metal oxide present in the absorbing agent and are supposed to be retained by said absorbing agent partly in the form of metal mercaptides and partly in the form of disulfurs R-S-S-R.

The first phase of the step of regeneration and cooling of the process according to the invention consists in sweeping the absorbing agent that has retained the mercaptans, that is, the absorbing agent loaded with metal mercaptides and disulfurs, by means of an inert hot gas for bringing said absorbing agent to a temperature comprised between 250° C. and 500° C., preferably between 300° C. and 450° C., and maintaining the absorbing agent at this temperature for a time sufficient for removing almost all the sulfurated compounds it contains so as to obtain an absorbing agent substantially free of sulfurated products.

The inert gas used for effecting said sweeping can be selected among the different gases having no action on the constituents of the absorbing agent. As examples of said gases there can be cited nitrogen, rare gases, $CO_2$, mixtures of said gases and even the purified gas resulting from the application of the process according to the invention to a gas containing mercaptans.

When the phase of sweeping the absorbing agent by the inert hot gas is finished, a gas containing free oxygen is put into contact with the absorbing agent free of the sulfurated compounds it contains for a time sufficient for completely reoxidizing the absorbing agent, that is, for re-forming the active metal oxide.

The concentration of free oxygen of the gas used for said reoxidation should not be too elevated in order to prevent a considerably increase of the temperature of the absorbing agent during this reoxidation. Satisfactory results are obtained when this concentration is comprised between 0.1 and 3% and more particularly between 0.5 and 1.5% by volume.

The gas that contains free oxygen can be formed by adding the appropriated amount of oxygen or air to the inert gas selected for effecting the phase of sweeping the absorbing agent that has retained the mercaptans.

It is possible simultaneously to carry out, on one hand, the contacting of the absorbing agent free of sulfurated compounds and having a temperature comprised between 250° C. and 500° C. with the gas containing the free oxygen in order to reoxidize said absorbing agent, and on the other hand, the largest part of the cooling phase of the absorbing agent using for said contacting a gas containing free oxygen which has a sufficiently low temperature, for example in the proximity of room temperature, and continuing this contacting until the temperature of the absorbing agent has been lowered to the desired value after which the regenerated cooled absorbing agent is swept by means of a cold inert gas selected from the same class as the inert gas used for sweeping the absorbing agent to be regenerated issued from the absorption step, until the absorbing agent contains no more absorbed oxygen.

It is preferable, however, first of all to contact the absorbing agent free of sulfurated compounds with the gas containing free oxygen while working at a temperature comprised between 250° C. and 500° C., particularly between 300° C. and 450° C., specially at a temperature substantially equal to that to which the absorbing agent has been brought in the course of its being swept by the hot inert gas, then cool the reoxidized absorbing agent to the temperature selected for the step of absorption by sweeping by means of a cold inert gas such as cited above, said gas having, for example, a temperature approximately room temperature.

The different phases of sweeping of the absorbing agent that are effected in the course of the step of regeneration and cooling of the absorbing agent can be carried out under pressures which, according to the requirements of rejection of the effluents of the sweeping operations, can be near the atmospheric pressure, for example from 1 to 5 bars, or can be substantially higher, specially from 10 to 15 bars or more, or even attain values on the order of from 40 to 100 bars.

The process according to the invention can be carried out in any installation including at least one reactor which contains an absorbing agent based on active metal oxide and that can alternatively function in absorption cycle and in the cycle of regeneration and cooling, as indicated before. To obtain an almost continuous operation of the process, use is advantageously made of an installation including at least two reactors situated parallel and containing an absorbing agent based on active metal oxide, the reactors being arranged to function alternatively in absorption cycle and in cyle of regeneration and cooling in a manner such that at least one of the reactors be in cycle of regeneration and cooling while the other reactor or reactors are in absorption cycle.

Figure 1:
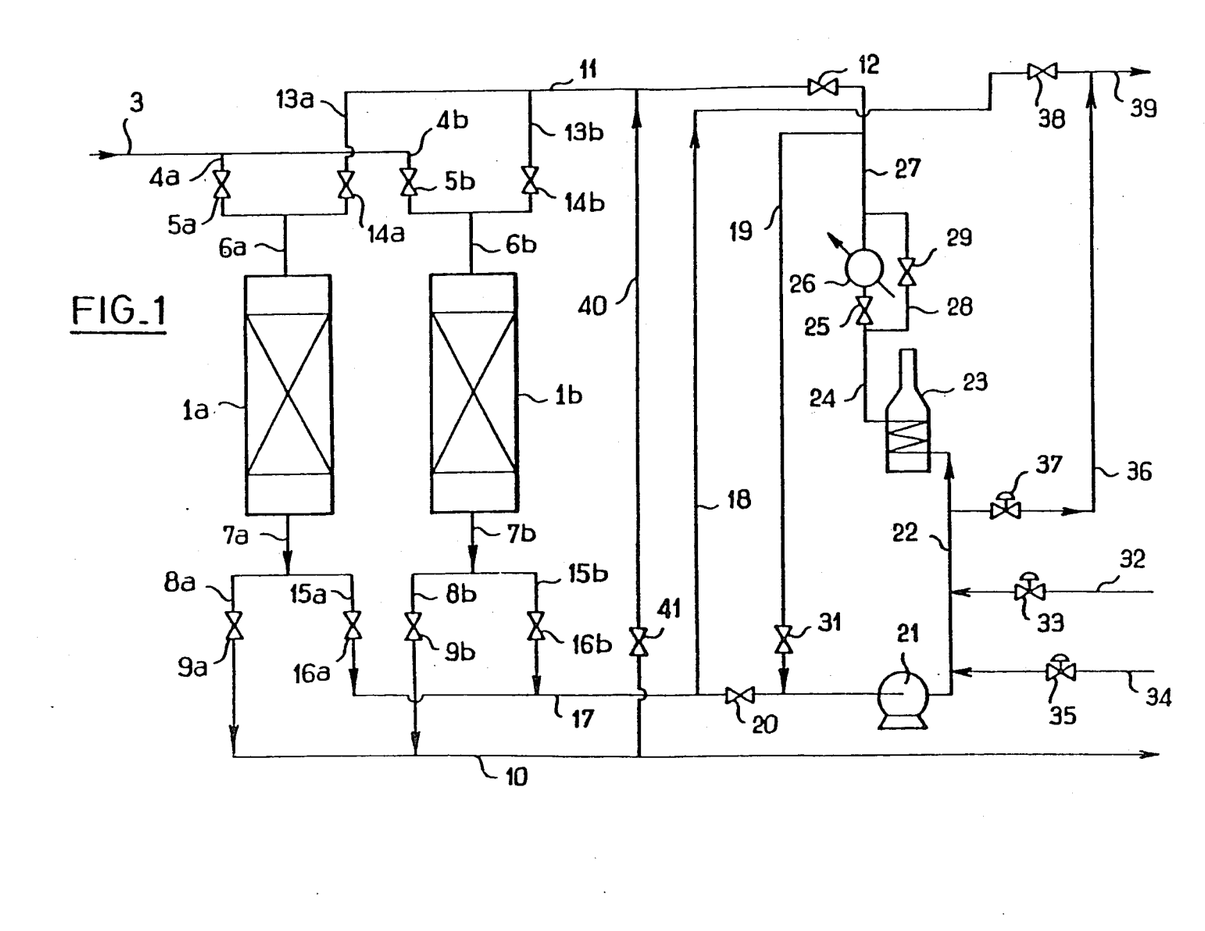
In FIGS. 1 to 3 of the attached drawing there are diagrammatically shown three examples of installations that can be used for carrying out almost continuously the process according to the invention.

Referring to FIG. 1, the installation includes two reactors 1a and 1b mounted in parallel and including each an appropriate amount of an absorbing agent based on active metal oxide. Each reactor is provided with an inlet conduit, respectively 6a and 6b, and with an outlet conduit, respectively 7a and 7b. The inlet conduit 6a of the reactor 1a is connected, on the one hand, by a conduit 4a provided with a gate valve 5a to a conduit 3 for introducing the gas to be treated and, on the other hand, by a conduit 13a provided with a gate valve 14a to a conduit 11 for introducing a regeneration gas and provided with a gate valve 12. The inlet conduit 6a of the reactor 1b is likewise connected, on the one hand, by a conduit 4b provided with a gate valve 5b to the conduit 3 for introducing the gas to be treated and, on the other hand, by a conduit 13b provided with a gate valve 14b to the conduit 11 for introducing the regeneration gas. The outlet conduit 7a of the reactor 1a is connected, on the one hand, by a conduit 8a provided with a gate valve 9a, to a conduit 10 of discharge of the purified gas and, on the other hand, by a conduit 15a provided with a gate valve 16a to a conduit 17 of recovery of the regeneration effluent connected by a gate valve 20 to the inlet of a blower 21. The outlet conduit 7b of the reactor 1b is likewise connected, on the one hand, by a conduit 8b provided with a gate valve 9b, to conduit 10 of discharge of the purified gas and, on the other hand, by a conduit 15b provided with a gate valve 16b, to conduit 17 of recovery of the regeneration effluent upstream of the gate valve 20. A shunt 40 provided with a gate valve 41 connects the conduit 10 to the conduit 11 downstream of the gate valve 12 mounted on the latter conduit. A conduit 18 provided with a gate valve 38 is likewise mounted as shunt on the conduit 17 upstream of the gate valve 20 and connects said conduit 17 to the conduit 39 for supplying a flare.

The exit of the blower 21 is connected by a conduit 22 to the inlet of a furnace 23 the exist of which is connected, by a conduit 24 provided with a gate valve 25, to the inlet of a condenser 26 the exit of which is connected by a conduit 27 to the conduit 11 upstream of the gate valve 12 mounted on the latter conduit. A conduit 28 provided with a gate valve 29 connects the conduit 24, upstream of the gate valve 25, to the conduit 27 and allows short-circuiting the condenser 26. The conduit 27 is likewise connected to the conduit 17, between the gate valve 20 mounted on said conduit and the blower 21, by a conduit 19 provided with a gate valve 31.

A coundnit 32 for introducing nitrogen, provided with a gate valve of variable delivery 33 and a conduit 34 for introducing air provided with a gate valve of variable delivery 35 are each connected to the conduit 22 while said conduit 22 is in addition connected by a conduit 36 provided with a gate valve 37 of variable delivery to the conduit 39 for supplying the flare.

The operation of this installation can be schematized as follows assuming the situation in which the reactor 1a has been put in absorption cycle while the reactor 1b is insulated in order to be subjected to the regeneration cycle.

In this situation the gate valves 5a, 9a, 29 and 31 are open while the gate valves 5b, 9b, 12, 14a, 14b, 16a, 16b, 25, 20, 33, 35, 37, 38 and 41 are closed.

The gas to be treated arrives by the conduit 3, traverses the conduit 4a of which the gate valve 5a is open, then the conduit 6a and penetrates in the reactor 1a where it comes into contact with the absorbing agent based on active metal oxide, the latter fixing the mercaptans contained in the gas. The purified gas exits from the reactor 1a by the conduit 7a, then traverses the conduit 8a of which the gate valve 9a is open to arrive at the discharge conduit 10.

On the other hand, an inert gas circulates in close circuit from the blower 21, passing by the conduit 22, the furnace 23, the portion of the conduit 24 going from the exit of the furnace 23 to the closed gate valve 25, the conduit 28 of which the gate valve 29 is open, the portion of the conduit 27 going from the conduit 28 to the conduit 19 of which the gate valve 31 is open, and the portion of the conduit 17 going from the conduit 19 to the blower 21.

From this moment the regeneration cycle of the absorbing agent contained in the reactor 1b is carried out as follows.

At first the gate valves 16b and 38 are open and the gas contained in the reactor 1b at absorption pressure escapes toward the conduit 39 for supplying the flare following the circuit formed by the conduit 7b, the conduit 15b of which the gate velve 16b is open, the portion of the conduit 17 going from the conduit 15b to the conduit 18, and the conduit 18 of which the gate valve 38 is open. This operation makes it possible to decompress the reactor 1b.

At the end of the decompression of the reactor 1b, the gate valves 31 and 38 are closed and the gate valves 12, 14b, 20, 33 and 37 are opened.

The inert gas reheated by passing into the furnace 23 crosses the conduit 11 of which the gate valve 12 is open, the conduit 13b of which the gate valve 14b is open, and the conduit 6b and penetrates into the reactor 1b where it ensures a sweeping of the absorbing agent charged with sulfur-containing products formed during the phase of absorption of the mercaptans. Said sweeping operation causes a desorption of the sulfur-containing products retained by the absorbing agent. The sweeping gas charged with desorbed sulfur-containing products exits from the reactor 1b by the conduit 7b, crosses the conduit 15b of which the gate valve 16b is open, and passes into the conduit 17 of which the gate valve 20 is open until the blower 21. The latter returns the sweeping gas it has received toward the furnace 23 through the conduit 22 and from the furnace toward the conduit 11, as indicated above. A portion of the sweeping gas containing the sulfur-containing products that are desorbed passing into the conduit 22 is directed by the conduit 36 with a delivery controlled by the gate valve 37, toward the conduit for supply of the flare 39. A corresponding delivery of pure nitrogen is injected in the conduit 22 by the conduit 32 through the gate valve 33 of controlled delivery.

Once the sweeping phase is terminated, the gate valves 33 and 37 are closed and the gate valve 35 is opened for admitting a controlled delivery of air in the circuit of gas passing by the reactor 1b, and said gas which then contains a controlled amount of oxygen as a function of the delivery of air introduced is made to circulate until complete reoxidation of the absorbing agent, that is, until re-formation of the active metal oxide.

At the end of this reoxidation of the absorbing agent, the gate valves 29 and 35 are closed, the gate valve 25 is opened and the furance 23 is stopped, which results, after quite a short duration, in sending into the reactor 1b a cold inert gas, which ensures the cooling of the reoxidized absorbing agent.

When the absorbing agent of the reactor 1b is cooled to the desired temperature, which generally corresponds to the one used for the absorption phase, the gate valves 12, 16b, 20 and 25 are closed and the gate valves 29, 31 and 41 are opened so as to isolate the reactor 1b from the circuit of inert gas of regeneration and to pass into the reactor a portion of the purified gas passing into the conduit 10 to ensure a recompression of the reactor 1b to the absorption pressure.

When the pressure in the reactor 1b reaches a value substantially equal to the absorption pressure, the gate valves 5b and 9b are opened to put the reactor 1b in absorption cycle and at the same time the gate valves 5a, 9a, 14b and 41 are closed to isolate the reactor 1a in order to regenerate the absorbing agent charged with the sulfur-containing products it contains, the regeneration being carried out as indicated above in the case of the reactor 1b by replacing the gate valves 5b, 9b, 14b and 16b by the gate valves 5a, 9a, 14a and 16a.

Figure 2:
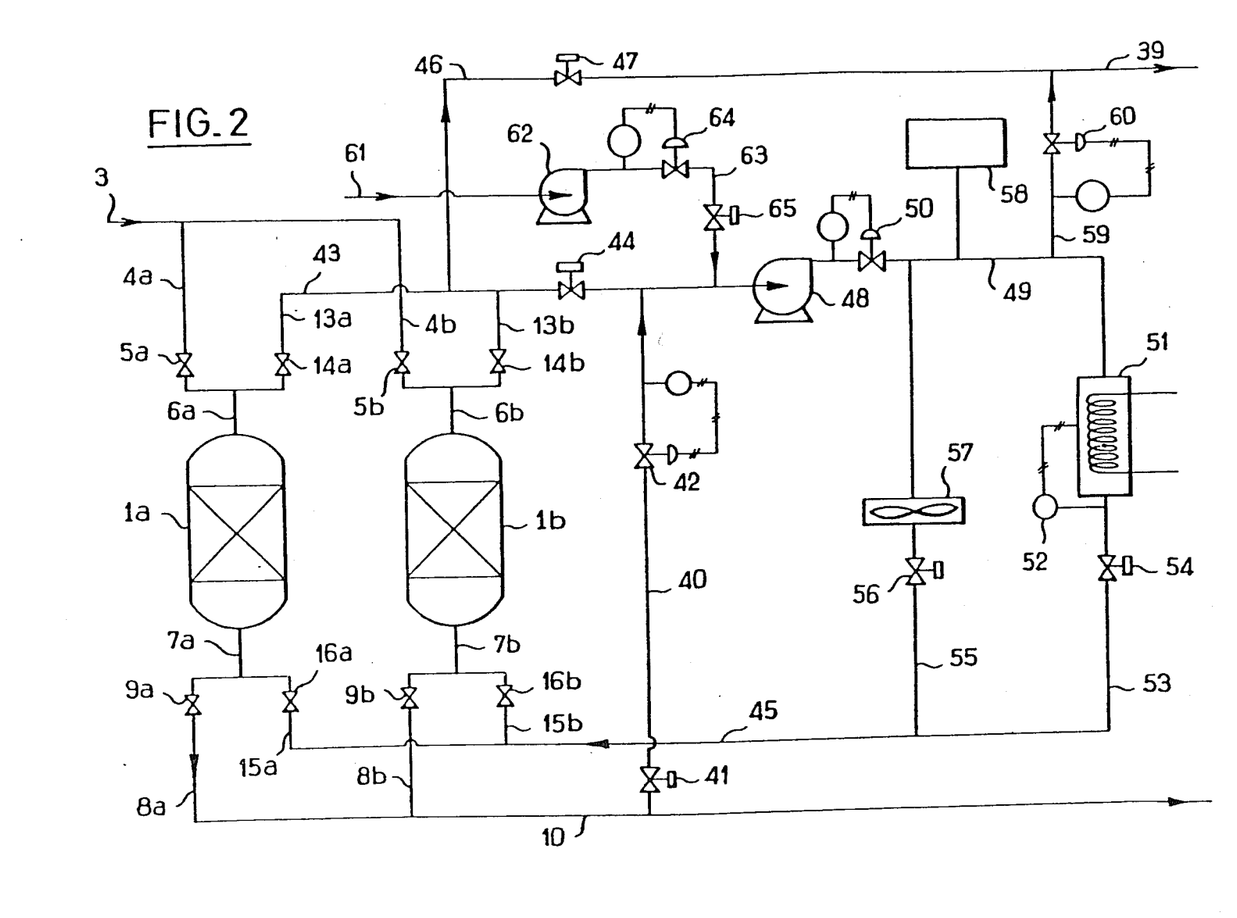

The installation shown in FIG. 2 includes two reactors 1a and 1b mounted in parallel and each one containing an appropriate amount of an absorbing agent based on active metal oxide. Each reactor is provided at one of its ends with a first conduit, respectively 6a and 6b, and at the other end with a second conduit, respectively 7a and 7b. The conduit 6a of the reactor 1a is connected, on the one hand, by a conduit 4a provided with a gate valve 5a, to a conduit 3 for introducing the gas to be treated and, on the other hand, by a conduit 13a provided with a gate valve 14a, to a conduit 43 of recovery of the regeneration effluent and provided with a gate valve 44. The conduit 6b of the reactor 1b is likewise connected, on the one hand, by a conduit 4b provided with a gate valve 5b, to the conduit 3 for introducing the gas to be treated and, on the other hand, by a conduit 13b provided with a gate valve 14b, to the conduit 43. The conduit 7a of the reactor is connected, on the one hand, by a conduit 8a provided with a gate valve 9a, to a conduit 10 for discharge of the purified gas and, on the other hand, by a conduit 15a provided with a gate valve 16a, to a conduit 45 for introducing a regeneration gas. The conduit 7b of the reactor 1b is likewise connected, on the one hand, by a conduit 8b provided with a gate valve 9b, to the conduit 10 of discharge of the purified gas and, on the other hand, by a conduit 15b provided with a gate valve 16b, to the conduit 45 for introducing the regeneration gas. A shunt 40 provided with a gate valve 41 and a gate valve 42 for regulation of pressure connects the conduit 10 to the conduit 41 downstream of the gate valve 44 mounted on the latter conduit. A conduit 46 provided with a gate valve 47 likewise is mounted as shunt on the conduit 43 upstream of the gate valve 44 and connects said conduit 43 to the conduit 39 for supply of a flare.

Downstream of the gate valve 44, the conduit 43 is connected to the inlet of a blower 48 the exit of which is connected by a conduit 49 provided with a gate valve 50 for delivery regulation to the inlet of an electric heater 51 equipped with a temperature regulator 52. The exit of the heater 51 is connected, by a conduit 53 provided with a gate valve 54, to the conduit 45 of introduction of the regeneration gas in the reactors 1a and 1b. A conduit 55 provided with a gate valve 56 and on which is mounted an aerocondenser 57 connects the conduit 45 to the conduit 49 downstream of the gate valve 50 and allows the short-circuiting of the heater 51. An oxygen analyzer 58 is mounted on the conduit 49 downstream of the junction of the latter with the conduit 55 and in addition a conduit 59 equipped with a gate valve 60 for pressure regulation connects the conduit 49, downstream of the analyzer 58, to the conduit 46 at the junction point of the latter with the conduit 39.

A conduit 61 for conveying air is connected at the inlet of a blower 62, the exit of which is connected by a conduit 63 provided with a gate valve 64 for regulation of the delivery and with a gate valve 65, to the conduit 43 downstream of the junction point of said conduit with the conduit 40.

The operation of this installation can be outlined as follows assuming the situation in which the reactor 1a has been put in absorption cycle while the reactor 1b is isolated in order to be subjected to the regeneration cycle.

In this situation the gate valves 5a, 9a, 41 and 54 are open while the gate valves 5b, 9b, 14a, 14b, 16a, 16b, 44, 47, 56 and 65 are closed.

The gas to be treated arrives by the conduit 3, traverses the conduit 4a, the gate valve 5a of which is open, the conduit 6a and penetrates in thereactor 1a where it comes into contact with the absorbing agent based on active metal oxide, the latter fixing the mercaptans contained in the gas. The purified gas exits from the reactor 1a by the conduit 7a, then traverses the conduit 8a, the gate valve 9a of which is open, to arrive at the discharge conduit 10.

The cycle of regeneration of the absorbing agent contained in the reactor 1b is carried out as follows.

At first the gate valves 14b and 47 are opened and the gas contained in the reactor 1b at absorption pressure escapes toward the conduit 39 for supplying the flare following the circuit formed by the conduit 6b, the conduit 13b, the gate valve 14b of which is open, and the conduit 46, the gate valve 47 of which is open. This operation makes it possible to decompress the reactor 1b.

At the end of the decompression of the reactor 1b, the gate valves 16b and 44 are opened.

The blower 48 absorbs the purified gas by the conduit 40 and directs said gas by the conduit 49 toward the heater 51 with a pressure controlled by the gate valve 50 for pressure regulation.

The gas re-heated by passing into the heater 51 traverses the conduit 53, the gate valve 54 of which is open, the conduit 45, then the conduit 15b, the gate valve 16b of which is open, and the conduit 7b, and penetrates in the reactor 1b where it ensures a sweeping of the absorbing agent charged with the sulfur-containing products formed during the phase of absorption of the mercaptans. This sweeping produces a desorption of the sulfur-containing products retained by the absorbing agent. The sweeping gas charged with the desorbed sulfur-containing products exits from the reactor 1b by the conduit 6b, traverses the conduit 13b, the gate valve 14b of which is open, and passes in part into the conduit 46, the gate valve 47 of which is open, until the conduit 39 for feeding the flare and in part into the conduit 43, the gate valve 44 of which is open, until the blower 48. The latter returns the gas it has received to the heater 51, as indicated above. In the course of this sweeping of the absorbing agent, the pressure of the gas caused to move by the blower 48 is kept constant either by adding purified gas retained on the conduit 10 by the conduit 40 if the pressure is low or by degasification by the conduit 59 toward the conduit 39 for feeding the flare if the pressure rises.

Once the sweeping phase is terminated, the gate valves 41 and 47 are closed and the gate valve 65 is opened for admitting a controlled delivery of air in the circuit of gas passing by the reactor 1b and the gas, which contains then a controlled amount of oxygen resulting from the delivery of air introduced, is made to circulate until complete reoxidation of the absorbing agent, that is, until the active metal oxide is re-formed.

At the end of this reoxidation of the absorbing agent, the gate valves 54 and 65 are closed, the gate valve 56 is opened, and the heater 51 is stopped, which after quite a short time results in sending to the reactor 1b a cold inert gas, which ensures the cooling of the reoxidized absorbing agent.

When the absorbing agent of the reactor 1b is cooled to the desired temperature, which generally corresponds to the one used for the absorption phase, the gate valves 14b and 44 are closed and the gate valve 41 is opened so as to admit in said reactor a portion of the purified gas passing into the conduit 10 for ensuring a recompression of the reactor 1b to the absorption pressure.

When the pressure in the reactor 1b reaches a value substantially equal to the absorption pressure, the gate valves 5b and 9b are opened to put the reactor 1b in absorption cycle and at the same time the gate valves 5a, 9a, 16b and 41 are closed to isolate the reactor 1a in order to regenerate the absorbing agent charged with the sulfur-containing products it contains, the regeneration being carried out as indicated above in the case of the reactor 1b, replacing the gate valves 5b, 9b, 14b and 16b by the gate valves 5a, 9a, 14a and 16a.

Figure 3:
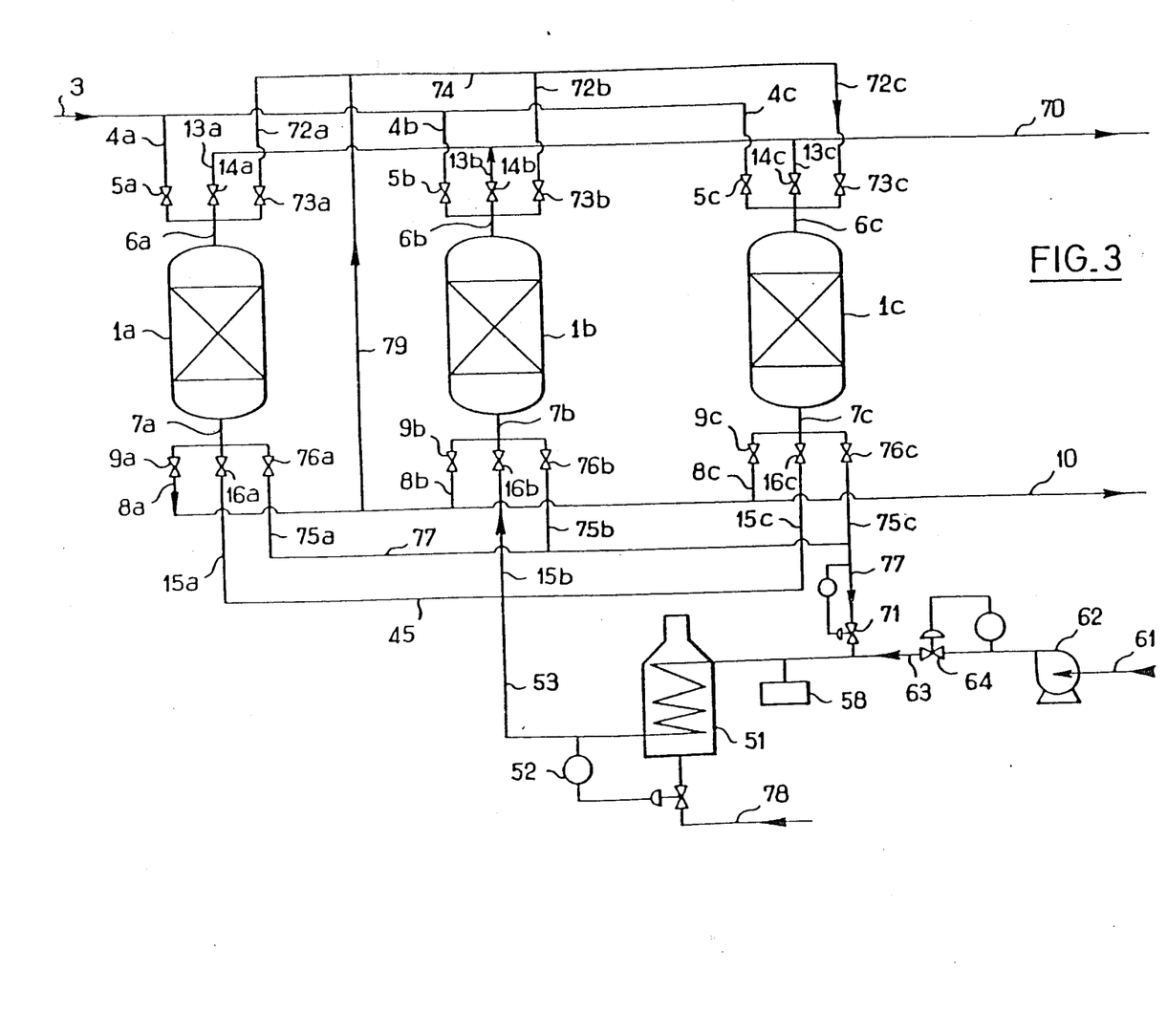

The installation shown in FIG. 3 includes three reactors 1a, 1b and 1c mounted in parallel and each one including an appropriated amount of an absorbing agent based on active metal oxide. Each reactor is provided at one of its ends with a first conduit, respectively 6a, 6b and 6c, and at the other end with a second conduit, respectively 7a, 7b and 7c. The conduit 6a of the reactor 1a is connected, on the one hand, by a conduit 4a provided with a gate valve 5a, to a conduit 3 for introducing the gas to be treated and, on the other hand, by a conduit 13a provided with a gate valve 14a, to a conduit 70 of recovery of the regeneration effluent, said conduit 6a being in addition connected by a conduit 72a provided with a gate valve 73a to a conduit 74 for introducing a cooling gas. The conduit 6b of the reactor 1b is likewise connected, on the one hand, by a conduit 4b provided with a gate valve 5b, to the conduit 3 for introducing the gas to be treated and, on the other hand, by a conduit 13b provided with a gate valve 14b, to the conduit 70 for recovery of the regeneration effluent and by a conduit 72b provided with a gate valve 73b to the conduit 74, while the conduit 6c of the reactor 1c is connected, on the one hand, by a conduit 4c provided with a gate valve 5c, to the conduit 3 and, on the other hand, by a conduit 13c provided with a gate valve 14c, to the conduit 70 and by a conduit 72c provided with a gate valve 73c, to the conduit 74. The conduit 7a of the reactor 1a is connected, on the one hand, by a conduit 8a provided with a gate valve 9a, to a conduit 10 for discharge of the purified gas and, on the other hand, by a conduit 15a provided with a gate valve 16a, to a conduit 45 for introducing a regeneration gas and by a conduit 75a provided with a gate valve 76a, to a conduit 77 for recovery of the cooling effluent. Conduit 45 is connected by a conduit 53 at the exit of a furnace 51 which is equipped with a temperature regulator 52 adjusting the delivery of fuel conveyed to the furnace by a conduit 75 while the conduit 77 is connected at the inlet of the furnace 51. The conduit 7b of the reactor 1b is likewise connected, on the one hand, by a conduit 8b provided with a gate valve 9b, to the conduit 10 for discharge of the purified gas and, on the other hand, by a conduit 15b provided with a gate valve 16b to the conduit 45 and by a conduit 75b provided with a gate valve 76b to the conduit 77, while the conduit 7c of the reactor 1c is connected, on the one hand, to the conduit 10 by a conduit 8c provided with a gate valve 9c and, on the other hand, to the conduit 45 by a conduit 15c provided with a gate valve 16c and to the conduit 77 by a conduit 75c provided with a gate valve 76c. A shunt 79 connects the conduit 10 to the conduit 74.

A conduit 61 for introducing air is connected at the inlet of a blower 62, the exit of which is connected by a conduit 63 provided with a gate valve 64 for pressure regulation, to the conduit 77 that conveys the cooling effluent to the furnace 51. An oxygen analyzer 58 is mounted on the conduit 77 between the junction of said conduit with the conduit 63 and the inlet of the furnace 51, while a gate valve 71 of pressure regulation is mounted on the conduit 77 between the junctions of said conduit with the conduit 75c and 63 respectively.

The operation of this installation can be outlined as follows assuming the situation in which the reactor 1a has been put in absorption cycle while the reactor 1b has been decompressed for being subjected to the regeneration cycle and the reactor 1c is in cooling phase.

In this situation are open the gate valves 5a and 9a of the reactor 1a, the gate valves 14b and 16b of the reactor 1b, and the gate valves 73c and 76c of the reactor 1c, while the other gate valves are closed.

The gas to be treated arrives by the conduit 3, traverses the conduit 4a, the gate valve 5a of which is open, then the conduit 6a and penetrates into the reactor 1a where it comes into contact with the absorbing agent based on active metal oxide, the latter fixing the mercaptans contained in the gas. The purified gas exits from the reactor 1a by the conduit 7a, then traverses the conduit 8a, the gate valve 9a of which is open, to arrive at the discharge conduit 10.

Part of the purified gas discharged by the conduit 10 and having a temperature close to room temperature is removed by the conduit 79 and conveyed by the conduit 74 and the conduit 72c, the gate valve 73c of which is open, to the reactor 1c which has just been regenerated. In this reactor said gas comes into contact with the hot regenerated absorbing agent and cools it. The effluent of the reactor 1c reaches the conduit 77 after having crossed the conduit 7c, then the conduit 75c, the gate valve 76c of which is open, and, after expansion by passing through the gate valve 71, it then penetrates in the furnace 51 where said effluent is re-heated to a temperature suitable for use in the regeneration. The re-heated gas issuing from the furnace 51 traverses the conduit 53, then the conduit 15b, the gate valve 16b of which is open, and the conduit 7b and penetrates in the reactor 1b where it ensures a sweeping of the absorbing agent charged with sulfur-containing products formed during the phase of absorption of the mercaptans. The sweeping produces a desorption of the sulfur-containing products retained by the absorbing agent. The sweeping gas charged with the desorbed sulfur-containing products issues from the reactor 1b by the conduit 6b, traverses the conduit 13b, the gate valve 14b of which is open, and passes into the conduit 70 for being directed toward an incinerator not shown.

Once the desorption of the sulfur-containing products is terminated, the gate valve 64 is opened for admitting a controlled delivery of air in the gas arriving at the furnace 51 by the conduit 77 and passing after re-heating by the reactor 1b and the injection of air is maintained in said gas until complete reoxidation of the absorbing agent, that is, until re-formation of the active metal oxide.

At the end of this reoxidation of the absorbing agent, the gate valve 64 of the conduit for introducing air is closed, then the gate valves 73c, 76c, 14b and 16b are closed and the gate valve 73b is opened. The pressure in the reactor 1b increases then and when it reaches a value approximate to the pressure of the purified gas, the gate valves 5a and 9a are closed and the gate valves 5c, 9c, 76b and 14a and then the gate valve 16a are opened when the reactor is decompressed. Following these different switchings of gate valves, the reactor 1c passes to the absorption phase while the reactor 1b passes to the cooling phase and the reactor 1a passes to the regeneration phase.

From the point of view of time the operations develop in a manner such that at every moment there is one reactor in absorption phase, one reactor in regeneration phase and one reactor in cooling phase and that each reactor be successively in absorption phase, in regeneration phase and in cooling phase.

The invention is illustrated by the examples that follow which are not limiting.

EXAMPLE 1

Working in an installation similar to the diagram in FIG. 1 of the appended drawing and operating as previously described, there was treated a commercial natural gas containing 150 v.p.m. methyl mercaptan, 50 v.p.m. propyl mercaptan, 5 p.p.m. H$_2$S and 2000 p.p.m. hydrocarbons having from C$_5$ to C$_8$.

For this treatment each one of the two reactors of the installation contained 6.5 m$^3$ of an absorbing agent appearing as small balls of about 5 mm diameter and consisting of an alumina impregnated with 10% by weight of cupric oxide by way of active metal oxide, said absorbing agent having a specific surface of about 190 m$^2$/g. The dynamic capacity of the new absorbing agent corresponded to the absorption of a quantity of sulfur-containing products of the mercaptans type representing, expressed as sulfur, 3.5 g per 100 g of absorbing agent.

The reactors functioned alternatively in absorption cycle and in regeneration cycle, as described above, using the operating conditions specified below.

| Absorption cycle | |
|---|---|
| Gas to be treated arriving by the conduit 3 and entering in the reactor in absorption phase | |
| Delivery | 41667 Nm$^3$/hour |
| Pressure | 70 bars |
| Absorption temperature | 30° C. |
| Duration of the absorption cycle | 12 hours |

| Regeneration cycle | |
|---|---|
| Decompression phase | |
| Duration | 15 minutes |
| Decompression speed | 5 bars/minute |
| Sweeping of the absorbing agent to be regenerated by the hot inert gas | |
| Delivery of the sweeping gas | 3850 Nm$^3$//hour |
| Temperature of the sweeping gas at the exit from the furnace 23 | 350° C. |
| Duration of the sweeping | 4h45mn |

| -continued | |
|---|---|
| Regeneration cycle | |
| Purge of gas by the gate valve 37 | 100 Nm$^3$/hour |
| Injection of nitrogen by the gate valve 33 | 100 Nm$^3$/hour |
| Reoxidation of the absorbing agent | |
| Duration | 2 hours |
| Temperature of the oxidation gas at the exit from furnace 23 | 350° C. |
| Concentration of oxygen in the reoxidation gas (maintained by controlled injection of air by the gate valve 35) | 1% by volume |
| Cooling of the reoxidized absorbing agent | |
| Duration | 4h45mn |
| Delivery of cooling gas | 3850 Nm$^3$/hour |
| Temperature of the cooling gas arriving by the conduit 11 | 30° C. |
| Recompression of the regenerated and cooled reactor by the purified gas | |
| Duration | 15 minutes |
| Recompression speed | 5 bars/minutes |

The purified gas discharged by the conduit 10 contained a total concentration of sulfur-containing products below 10 v.p.m.

After 150 absorption and regeneration cycles, the dynamic capacity of the regenerated absorbing agent was still practically equal to that of the new absorbing agent.

EXAMPLE 2

Working in an installation similar to the diagram in FIG. 2 of the appended drawing and operating as described above, there was treated a commercial natural gas containing 52 v.p.m. methyl mercaptan, 18 v.p.m. propyl mercaptan, 5 p.p.m. H$_2$S and 2000 p.p.m. hydrocarbons of from C$_5$ to C$_8$.

For this treatment each one of the two reactors of the installation contained 1.5 ton of an absorbing agent identical with the one in example 1.

The reactors functioned alternatively in absorption cycle and in regeneration cycle as described with reference to FIG. 2 using the operating conditions specified below.

| Absorption cycle: | |
|---|---|
| Gas to be treated arriving by the conduit 3 and entering in the reactor in absorption phase | |
| Delivery | 41667 Nm$^3$/hour |
| Pressure | 70 bars |
| Absorption temperature | 30° C. |
| Duration of the absorption cycle | 12 hours |

| Regeneration cycle: | |
|---|---|
| Decompression phase | |
| Duration | 15 minutes |
| Decompression speed | 5 bars/minutes |
| Sweeping of the absorbing agent to be regenerated by the hot inert gas | |
| Delivery of the sweeping gas | 1500 Nm$^3$/hour |
| Temperature of the sweeping gas at the exit of the heater 51 | 350° C. |
| Duration of the sweeping | 3 hours |
| Reoxidation of the absorbing agent | |
| Duration | 2 hours |

-continued

| Regeneration cycle: | |
|---|---|
| Temperature of the reoxidation gas at the exit of heater 51 | 350° C. |
| Concentration of oxygen in the reoxidation gas (maintained by controlled injection of air by the conduit 63) | 1.5% by volume |
| Cooling of the reoxidized absorbing agent | |
| Duration | 6.5 hours |
| Delivery of cooling gas | 750 Nm$^3$/hour |
| Temperature of the cooling gas arriving by the conduit 55 | 30° C. |
| Recompression of the regenerated and cooled reactor by the purified gas | |
| Duration | 15 minutes |
| Recompression speed | 5 bars/minutes |

The purified gas discharged by the conduit 10 contained a total concentration of sulfur of less than 2 mg/Nm$^3$.

EXAMPLE 3

Working in an installation similar to the diagram in FIG. 3 of the appended drawing, and operating as described above, there was treated a commercial natural gas containing 52 v.p.m. methyl mercaptan, 18 v.p.m. propyl mercaptan, 5 p.p.m. H$_2$S and 2000 p.p.m. hydrocarbons from C$_5$ to C$_8$.

For this treatment each one of the three reactors of the installation contained 1.5 ton of an absorbing agent identical with the one used in example 1.

The reactors functioned successively in absorption cycle, in regeneration cycle and in cooling cycle as described with reference to FIG. 3 using the operating conditions specified below.

| Absorption cycle: | |
|---|---|
| Gas to be treated arriving by conduit 3 and entering in the reactor in absorption phase | |
| Delivery | 41667 Nm$^3$/hour |
| Pressure | 70 bars |
| Absorption temperature | 30° C. |
| Duration of the absorption cycle | 12 hours |

| Regeneration cycle: | |
|---|---|
| Decompression phase | |
| Duration | 1 hour |
| Decompression speed | 1.15 bar/minute |
| Sweeping of the absorbing agent to be regenerated by the hot regeneration gas | |
| Delivery of the sweeping gas | 750 Nm$^3$/hour |
| Temperature of the sweeping gas at the exit of the furnace 51 | 350° C. |
| Duration of the sweeping | 6 hours |
| Reoxidation of the absorbing agent | |
| Duration | 4 hours |
| Temperature of the reoxidation gas at the exit of the furnace 51 | 350° C. |
| Concentration of oxygen in the reoxidation gas (maintained by controlled injection of air by the conduit 64) | 1% by volume |
| Recompression of the regeneratd reactor by the purified gas | |
| Duration | 1 hour |

| Regeneration cycle: | |
|---|---|
| Recompression speed | 1.15 bar/minute |

| Cooling cycle: | |
|---|---|
| Cooling of the reoxidized absorbing agent | |
| Duration | 12 hours |
| Delivery of cooling gas | 750 Nm$^3$/hour |
| Temperature of the cooling gas arriving by the conduit 74 | 30° C. |

The purified gas discharged by the conduit 10 contained a total concentration of sulfur of less than 2 mg/Nm$^3$.

We claim:

1. In a regenerative process for the removal of mercaptans contained in a gas by contacting the gas with a solid absorbing agent containing at least one active metal oxide selected from the group consisting of oxides of copper, zinc, cadmium, mercury, iron, cobalt, silver, platinum and lead, said oxide capable of retaining the mercaptans on said absorbing agent, and regenerating said solid absorbing agent with a gas containing free oxygen to oxidize said absorbing agent and regenerate it, and cooling said regenerated absorbing agent to a temperature appropriate for the absorption step the improvement which comprises:

(a) bringing said absorbing agent, that has retained the mercaptans to a temperature between 250° C. and 500° C. by sweeping the absorbing agent with a hot inert gas selected from the group consisting of nitrogen, rare gases, carbon dioxide, mixtures thereof, and the purified gas produced by the process, and continuing said sweeping substantially at said temperature until said absorbing agent is substantially free of sulfurated compounds;

(b) contacting the absorbing agent with a gas containing free oxygen, at a temperature below 500° C. to oxidize said absorbing agent;

(c) contacting the oxidized absorbing agent with an inert gas to remove free oxygen contained in said absorbing agent prior to use in the absorption step; and (d) absorbing the sulfurated compounds at a temperature below 100° C.

2. A process according to claim 1, wherein the absorbing agent that has retained the mercaptans is brought to a temperature comprised between 300° C. and 450° C. by sweeping with the hot inert gas prior to contact with the gas containing the free oxygen.

3. A process according to claim 1, wherein the gas to be treated contains a total amount of mercaptans not greater than 2% by volume of said gas.

4. A process according to claim 1, wherein the mercaptans contained in the gas to be treated correspond to the formula RSH, wherein R designates a hydrocarbon radical having from one to eight carbon atoms.

5. A process according to any one of claim , wherein said absorbing agent comprises by at least one active metal oxide associated with a porous inert carrier, said carrier being a porous metal oxide chemically inert to the mercaptans.

6. A process according to claim 5, wherein said absorbing agent has a specific surface area, determined by the BET method, of from 10 to 500 m²/g.

7. A process of claim 5, wherein the porous carrier is alumina.

8. A process of claim 5, wherein said absorbing agent has a specific surface area determined by the BET method of from 100 to 300 m²/g.

9. A process according to claim 5, wherein the total amount of active metal oxide in said absorbing agent represents from 1 to 30% by weight of said absorbing agent.

10. A process of claim 9, wherein the active metal oxide in said absorbing agent represents from 5 to 20% by weight of said absorbing agent.

11. A process according to claim 1, wherein absorption step is carried out at temperatures of from 5° to 70° C.

12. A process according to claim 1, wherein the pressure in the absorption step is from 2 to 80 bars.

13. A process of claim 12, wherein the absorption step is carried out at a pressure of from 5 bars to 40 bars.

14. A process according to claim 1, wherein the period of time of contact of the gas to be treated with said absorbing agent, in the course of the absorption step, is from 0.5 to 10 seconds.

15. A process according to claim 1, wherein the gas containing free oxygen for oxidizing said absorbing agent has a concentration of free oxygen comprised between 0.1 and 3% by volume.

16. A process of claim 15, wherein the gas containing free oxygen for oxidizing the absorbing agent comprises between 0.5 and 1.5% by volume of free oxygen.

17. A process according to claim 1, wherein contacting the absorbing agent, substantially free of sulfurated compounds, with the gas containing the free oxygen to oxidize the absorbing agent and most of the phase of cooling the absorbing agent are carried out by contacting the absorbing agent with a gas containing free oxygen, the temperature of which is close to room temperature, after which the cooled regenerated absorbing agent is swept by means of a cold inert gas.

18. A process according to claim 1, wherein the contacting of the absorbing agent, substantially free of sulfurated compounds, with the gas containing free oxygen is carried out at a temperature comprised of between 250° C. and 500° C., substantially equal to that to which said absorbing agent has been brought in the course of its being swept by the hot inert gas, the cooled absorbing agent, oxidized by sweeping, is cooled by means of a cold inert gas, said gas having a temperature equal to approximately room temperature.

19. A process of claim 1, wherein the absorption step is carried out at a temperature of from 20° C. to 50° C.

20. A process of claim 1, wherein the absorbing agent substantially free of sulfur-containing compounds is contacted with the gas containing free oxygen at a temperature between 300° C. and 450° C.

21. In a regenerative process for the removal of mercaptans contained in a gas by contacting the gas with a solid absorbing agent containing at least one active metal oxide selected from the group consisting of oxides of copper, zinc, cadmium, mercury, iron, cobalt, silver, platinum and lead, said oxide capable of retaining the mercaptans on said absorbing agent, and regenerating said solid absorbing agent with a gas containing free oxygen to oxidize said absorbing agent and regenerate it, and cooling said regenerated absorbing agent to a temperature appropriate for the absorption step, the improvement which comprises:

(a) bringing said absorbing agent that has retained the mercaptans, to a temperature between 250° C. and 500° C. by sweeping the absorbing agent with a hot inert gas which is inert to both the mercaptan absorbing agent and to the sulfur materials being removed from said absorbing agent, and continuing said sweeping substantially at said temperature until said absorbing agent is substantially free of sulfurated compounds;

(b) contacting the absorbing agent with a gas containing free oxygen, at a temperature below 500° C. to oxidize said absorbing agent;

(c) contacting the oxidized absorbing agent with an inert gas to remove free oxygen contained in said absorbing agent prior to use in the absorption step; and (d) absorbing the sulfurated compounds at a temperature below 100° C.

* * * * *